(12) United States Patent
Mori et al.

(10) Patent No.: US 10,940,331 B2
(45) Date of Patent: Mar. 9, 2021

(54) MEDICAL APPARATUS AND METHOD

(71) Applicant: Toshiba Energy Systems & Solutions Corporation, Kawasaki (JP)

(72) Inventors: Shinichiro Mori, Chiba (JP); Keiko Okaya, Setagaya (JP); Ryusuke Hirai, Shinagawa (JP); Fumi Maruyama, Miura (JP); Koki Yanagawa, Tokorozawa (JP)

(73) Assignee: Toshiba Energy Systems & Solutions Corporation, Kawasaki (JP)

( * ) Notice: Subject to any disclaimer, the term of this patent is extended or adjusted under 35 U.S.C. 154(b) by 169 days.

(21) Appl. No.: 16/223,436

(22) Filed: Dec. 18, 2018

(65) Prior Publication Data

US 2019/0184198 A1  Jun. 20, 2019

(30) Foreign Application Priority Data

Dec. 20, 2017  (JP) .............................. JP2017-244073

(51) Int. Cl.
  *A61N 5/10* (2006.01)
  *G06T 7/70* (2017.01)
  *G06T 7/246* (2017.01)
  *G06T 7/30* (2017.01)

(52) U.S. Cl.
  CPC ......... *A61N 5/1049* (2013.01); *A61N 5/1064* (2013.01); *G06T 7/248* (2017.01); *G06T 7/30* (2017.01); *G06T 7/70* (2017.01); *A61N 5/1065* (2013.01); *A61N 5/1068* (2013.01); *A61N 2005/1061* (2013.01); *A61N 2005/1062* (2013.01); *A61N 2005/1074* (2013.01); *G06T 2207/10076* (2013.01); *G06T 2207/10081* (2013.01); *G06T 2207/10121* (2013.01);
(Continued)

(58) Field of Classification Search
  None
  See application file for complete search history.

(56) References Cited

U.S. PATENT DOCUMENTS 7,620,146 B2 * 11/2009 Mostafavi ............ A61B 6/4441
  378/62
2005/0053196 A1  3/2005 Mostafavi
(Continued)

FOREIGN PATENT DOCUMENTS

JP  2017-144000  8/2017

*Primary Examiner* — Hoon K Song
(74) *Attorney, Agent, or Firm* — Oblon, McClelland, Maier & Neustadt, L.L.P.

(57) ABSTRACT

A medical apparatus according to an embodiment includes an acquirer, a corrector, an identifier, and an output controller. The acquirer is configured to acquire a fluoroscopic image of an object from an imager. The corrector is configured to correct an image of one or more predetermined regions used for identifying a target position of the object in the fluoroscopic image based on one or more correction values but does not correct an image of at least a part of a region out of the predetermined region in the fluoroscopic image. The identifier is configured to identify the target position based on an image corrected by the corrector. The output controller is configured to output an irradiation permission signal to a therapeutic device which irradiates the object with a therapeutic beam based on the target position identified by the identifier.

18 Claims, 10 Drawing Sheets

(52) U.S. Cl.
CPC .............. *G06T 2207/10124* (2013.01); *G06T 2207/20081* (2013.01); *G06T 2207/30096* (2013.01)

(56) References Cited

U.S. PATENT DOCUMENTS

2016/0082284 A1    3/2016    Ooga et al.
2017/0231586 A1    8/2017    Hirai et al.

\* cited by examiner

MEDICAL APPARATUS AND METHOD

CROSS-REFERENCE TO RELATED APPLICATION

This application is based upon and claims the benefit of priority from Japanese Patent Application No. 2017-244073, filed Dec. 20, 2017; the entire content of which is incorporated herein by reference.

BACKGROUND OF THE INVENTION

Field of the Invention

Embodiments described herein relate generally to a medical apparatus and a method.

Description of Related Art

Therapeutic devices which irradiate a patient (object) with a therapeutic beam such as a heavy particle beam are known. There are cases in which a lesion of an object, that is, a spot to be irradiated with a therapeutic beam moves due to respirations, heartbeat, intestinal movements, and the like (hereinafter, these will be collectively referred to as "respirations and the like"). As a therapeutic method suitable therefor, a gated irradiation method and a tracking irradiation method are known.

When a lesion which moves due to respirations is irradiated with a therapeutic beam, there is a need to perform irradiation synchronously with respiratory phases of an object. Techniques of respiratory phase synchronization include a technique of ascertaining the respiratory phase (external respiratory synchronization) by utilizing an output value of a sensor attached to the body of an object, and a technique of ascertaining the respiratory phase (internal respiratory synchronization) based on a fluoroscopic image of an object. The processing for respiratory phase synchronization is performed by a medical apparatus which outputs a control signal to a therapeutic device. For example, a medical apparatus controls a therapeutic device by performing wired or wireless communication with the therapeutic device.

Incidentally, medical apparatus are required to grasp the ever-changing position of a target of an object without a significant delay in time. However, there is physical constraint in the information processing speed of electronic instruments, without being limited to medical apparatus. Therefore, in technologies in the related art, when a fluoroscopic image needs to be corrected, information processing cannot catch up, and it is sometimes difficult to grasp the position of a target of an object without a significant delay.

SUMMARY OF THE INVENTION

An object to be achieved by the present invention is to provide a medical apparatus and a method, which can grasp a position of a target of an object without a significant delay even when a fluoroscopic image needs to be corrected.

A medical apparatus according to an embodiment includes an acquirer, a corrector, an identifier, and an output controller. The acquirer acquires a fluoroscopic image of an object from an imager which performs imaging by irradiating the object with an electromagnetic wave to generate a fluoroscopic image. The corrector corrects an image of one or more predetermined regions used for identifying a target position of the object in the fluoroscopic image based on one or more correction values but does not correct an image of at least a part of a region out of the predetermined region in the fluoroscopic image. The identifier identifies the target position based on an image corrected by the corrector. The output controller outputs an irradiation permission signal to a therapeutic device which irradiates the object with a therapeutic beam based on the target position identified by the identifier.

According to the present embodiment, it is possible to provide a medical apparatus and a method, which can grasp a position of a target of an object without a significant delay even when a fluoroscopic image needs to be corrected.

DETAILED DESCRIPTION OF THE INVENTION

Hereinafter, a medical apparatus and a control method for a medical apparatus according to embodiments will be described with reference to the drawings. In this application, the expression "based on XX" denotes "based on at least XX" and also includes a case based on another element in addition to XX. The expression "based on XX" is not limited to a case of directly adopting XX and also includes a case based on a result realized by performing computation or processing with respect to XX. The term "XX" indicates an arbitrary element (for example, arbitrary information).

First Embodiment

<Configuration>

Figure 1:
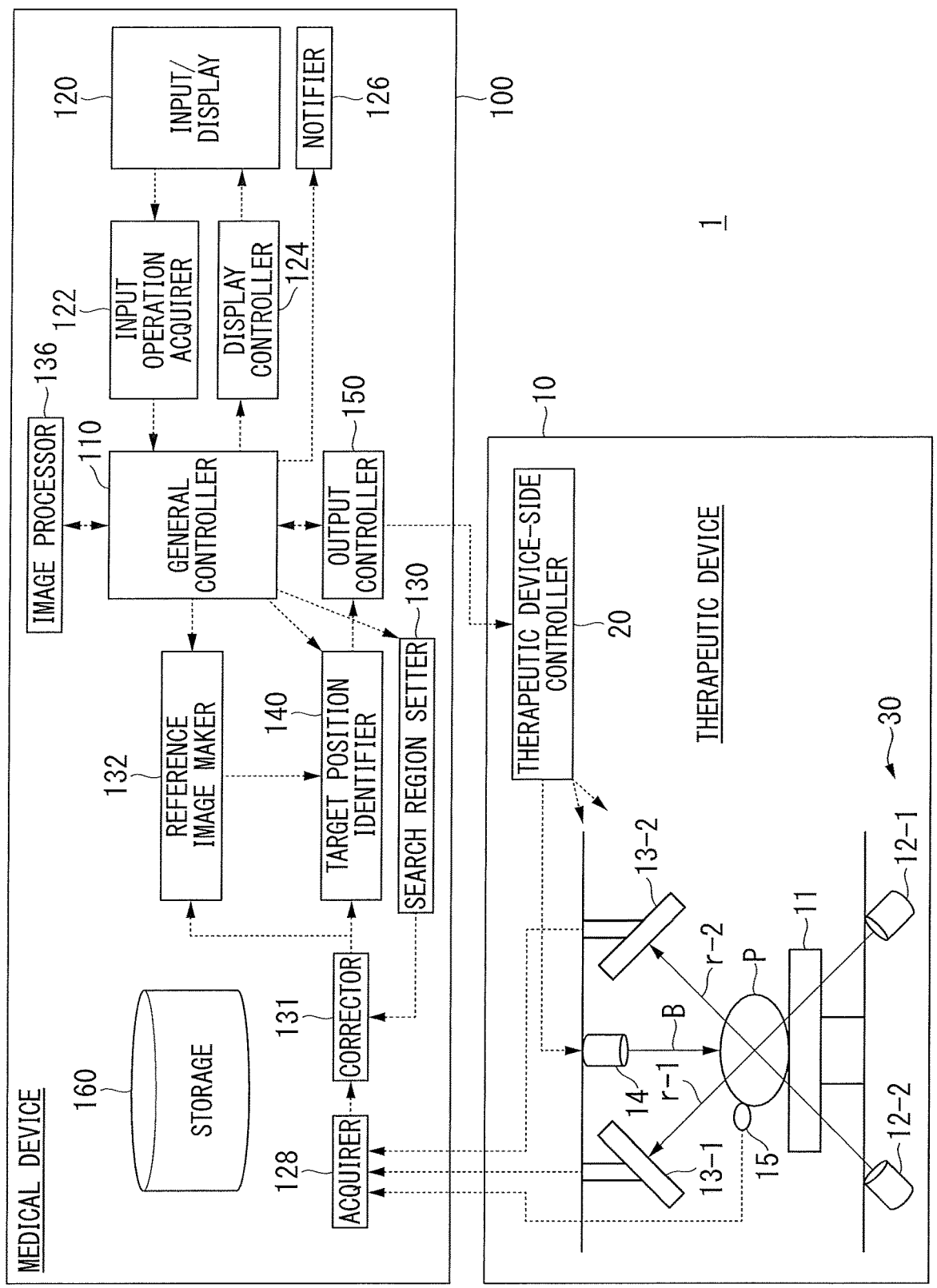
FIG. 1 is a configuration diagram of a therapy system including a medical apparatus according to a first embodiment.

FIG. 1 is a configuration diagram of a therapy system 1 including a medical apparatus 100 of a first embodiment. For example, the therapy system 1 includes a therapeutic device 10 and the medical apparatus 100.

For example, the therapeutic device 10 includes a bed 11, radiation sources 12-1 and 12-2, detectors 13-1 and 13-2, an irradiation gate 14, a sensor 15, and a therapeutic device-side controller 20. Hereinafter, a hyphen and a numeral following it in the reference sign indicate a fluoroscopic radiation or a fluoroscopic image realized by a set of a radiation source and a detector. Suitably, the hyphen and the numeral following it in the reference sign may be omitted in description.

An object P to be treated is fixed to the bed 11. The radiation source 12-1 irradiates the object P with a radiation r-1. The radiation source 12-2 irradiates the object P with a radiation r-2 at an angle different from that of the radiation source 12-1. The radiations r-1 and r-2 are examples of electromagnetic waves and are X-rays, for example. Hereinafter, description will be given on this premise.

The radiation r-1 is detected by the detector 13-1. The radiation r-2 is detected by the detector 13-2. For example, the detectors 13-1 and 13-2 are flat panel detectors (FPD), image intensifiers, or color image intensifiers. The detector 13-1 detects energy of the radiation r-1, performs digital conversion, and outputs the conversion result to the medical apparatus 100 as a fluoroscopic image TI-1. The detector 13-2 detects energy of the radiation r-2, performs digital conversion, and outputs the conversion result to the medical apparatus 100 as a fluoroscopic image TI-2. In FIG. 1, two sets of the radiation source and the detector are illustrated. However, the therapeutic device 10 may include three or more sets of the radiation source and the detector. Hereinafter, the radiation sources 12-1 and 12-2 and the detectors 13-1 and 13-2 will be generically referred to as an imager 30.

In a therapy stage, the irradiation gate 14 irradiates the object P with a therapeutic beam B. Examples of the therapeutic beam B include at least one of a heavy particle beam, an X-ray, a γ-ray, an electron beam, a proton beam, and a neutron beam. In FIG. 1, only one irradiation gate 14 is illustrated. However, the therapeutic device 10 may include a plurality of irradiation gates.

The sensor 15 is a sensor for recognizing an external respiratory phase of the object P and is attached to the body of the object P. For example, the sensor 15 is a pressure sensor. Detection results of the sensor 15 are output to the medical apparatus 100.

The therapeutic device-side controller 20 operates the radiation sources 12-1 and 12-2, the detectors 13-1 and 13-2, and the irradiation gate 14 in response to a control signal from the medical apparatus 100.

For example, the medical apparatus 100 includes a general controller 110, an input/display 120, an input operation acquirer 122, a display controller 124, an acquirer 128, a search region setter 130, a corrector 131, a reference image maker 132, an image processor 136, a target position identifier 140, an output controller 150, and a storage 160. For example, at least a part of the general controller 110, the input operation acquirer 122, the display controller 124, the acquirer 128, the search region setter 130, the corrector 131, the reference image maker 132, the image processor 136, the target position identifier 140, and the output controller 150 is realized by a hardware processor such as a central processing unit (CPU) or a graphics processing unit (GPU) executing a program (software) stored in the storage 160. A part or all of these constituent elements may be realized by hardware (circuit section; including circuitry) such as a large scale integration (LSI), an application specific integrated circuit (ASIC), or a field-programmable gate array (FPGA) or may be realized by cooperation of software and hardware. These are also similarly applied to a reference image maker 132A (second embodiment) and a target identifier 140B (third embodiment) described below.

Hereinafter, the function of each part of the medical apparatus 100 will be described. In description of the medical apparatus 100, unless otherwise identified, processing performed with respect to the fluoroscopic image TI will be regarded to be executed in parallel with both the fluoroscopic images TI-1 and TI-2. The general controller 110 generally controls the functions of the medical apparatus 100.

For example, the input/display 120 includes a display device such as a liquid crystal display (LCD), an organic electroluminescence (EL) display device, or a light emitting diode (LED) display; and an input device which receives an input operation performed by an operator. The input/display 120 may be a touch panel in which a display device and an input device are integrally formed or may include an input device such as a mouse and a keyboard. The input/display 120 is an example of "a display".

The input operation acquirer 122 recognizes the details of an operation (touching, flicking, swiping, clicking, dragging, key-inputting, or the like) performed with respect to the input/display 120 and outputs the details of the recognized operation to the general controller 110.

For example, the display controller 124 causes the input/display 120 to display an interface screen for receiving an instruction to start each stage of a therapy (which will be described below). Moreover, the display controller 124 causes the input/display 120 to display a screen showing states of the object P, the therapeutic device 10, and the medical apparatus 100 in a checking stage before irradiation of the therapeutic beam B, and an irradiation stage of the therapeutic beam B. Here, displaying an image includes generation of elements of an image based on computation results, and allocation of elements of an image made in advance to a display screen.

The acquirer 128 acquires the fluoroscopic image TI from the imager 30. The acquirer 128 acquires a detection value of the sensor 15. Moreover, the acquirer 128 acquires three-dimensional volume data of the object P from a medical inspection device (not illustrated). Examples of three-dimensional volume data include three-dimensional CT (Computed Tomography) images. In the present embodiment, time-series three-dimensional CT images will be referred to as "4D CT images".

The search region setter 130 sets a search region with respect to the fluoroscopic image TI acquired by the acquirer 128. The search region is a region in which a target position (which will be described below) is searched for in the fluoroscopic image TI acquired by the acquirer 128. The corrector 131 performs correction (alignment correction) with respect to the fluoroscopic image TI acquired by the acquirer 128. When all or a part of the fluoroscopic images TI is used as a reference image to identify the target position, the reference image maker 132 generates a reference image to be used for markerless tracking, based on the fluoroscopic image TI corrected by the corrector 131. The details of these will be described below in detail.

The image processor 136 performs image processing such as deformable registration and a digitally reconstructed radiograph (DRR) image generation. Deformable registration is processing performed with respect to time-series three-dimensional volume data, in which positional information designated for three-dimensional volume data at a certain point of time is deployed in three-dimensional volume data at another point of time. A DRR image is a virtual fluoroscopic image generated by irradiating three-dimensional volume data with a radiation from a virtual radiation source.

The target position identifier 140 identifies the target position based on the fluoroscopic image TI corrected by the corrector 131. For example, the target position identifier 140 identifies the target position in the fluoroscopic image TI corrected by the corrector 131. "A target" may be a lesion of the object P, that is, a part to be irradiated with the therapeutic beam B, or may be a marker or a characteristic spot of the object P. Since the difference between a characteristic spot such as the diaphragm, the heart, or a bone and surrounding spots appears in a relatively clear manner in the fluoroscopic image TI, the characteristic spot is a spot of which the position can be easily identified when a computer analyzes the fluoroscopic image TI. "A target position" is a position of a target. That is, the target position may be a position of a lesion of the object P, or may be a marker or a position of a characteristic spot of the object P. The target position may be one point or a region having a two-dimensional or three-dimensional spread.

The output controller 150 outputs an irradiation permission signal to the therapeutic device 10 based on the target position identified by the target position identifier 140. For example, in a gated irradiation method, when the target position identified by the target position identifier 140 is settled within a gating window, the output controller 150 outputs a gate-on signal to the therapeutic device 10. A gating window is a region set in a two-dimensional plane or a three-dimensional space. A gating window is a region showing that irradiation of the therapeutic beam B may be performed when the target position is settled within this gating window, and is an example of "an irradiation permission range". A gate-on signal is a signal for instructing the therapeutic device 10 to irradiate the object P with the therapeutic beam B. A gate-on signal is an example of "an irradiation permission signal". The therapeutic device 10 performs irradiation of the therapeutic beam B when a gate-on signal is input, and does not perform irradiation of the therapeutic beam B when no gate-on signal is input. The irradiation permission range is not limited to a fixedly set range and may be a range which moves in a manner following a movement of a lesion.

For example, the storage 160 is realized by a random access memory (RAM), a read only memory (ROM), a hard disk drive (HDD), or a flash memory. The storage 160 stores time-series three-dimensional volume data, the fluoroscopic images TI, output values of the sensor 15, and the like are stored, in addition to the program described above.

Next, some function units of the medical apparatus 100 will be described in detail.

<Search Region Setter 130>

Figure 2:
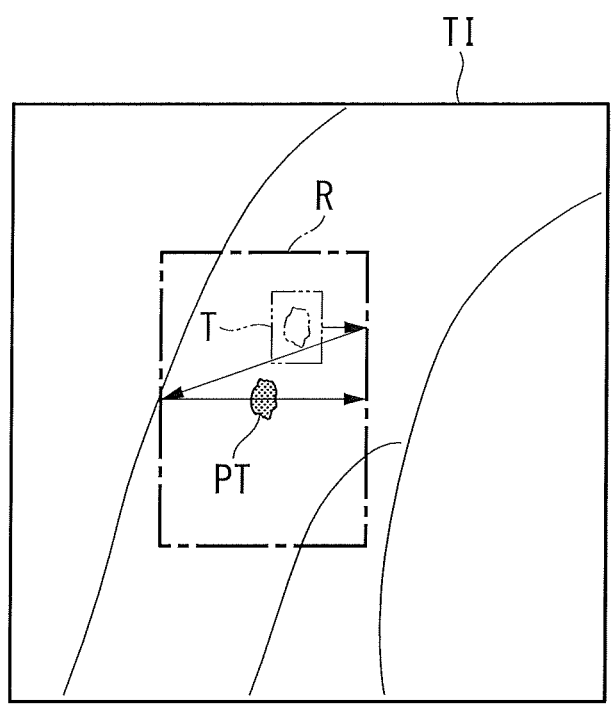
FIG. 2 is a view illustrating an example of a search region and a template superimposed on a fluoroscopic image of the first embodiment.

The search region setter 130 sets the position and the size of the search region with respect to the fluoroscopic image TI acquired by the acquirer 128. FIG. 2 is a view illustrating an example of a search region R and a template T superimposed on the fluoroscopic image TI. For the sake of convenience of description, FIG. 2 illustrates an image which is not corrected by the corrector 131. However, actually, searching for a target position PT is performed based on an image corrected by the corrector 131 as described below.

Here, movement of the target position PT due to respirations and the like is limited to the inside of the range which is within the fluoroscopic image TI. Therefore, the search region setter 130 sets only a part of the region in the fluoroscopic image TI as the search region R. In the present embodiment, the search region R is a region including the target position PT. The search region R is an example of "a region used for identifying the target position". For example, in markerless tracking, the search region R is an example of a region in which the target position PT is determined by the target position identifier 140, using a reference image generated by the reference image maker 132. In the present embodiment, in markerless tracking, the search region R is a region in which the target position PT is searched for through template matching performed by the target position identifier 140 using the template T generated by the reference image maker 132. The template T is an example of "a reference image used for markerless tracking". However, "a reference image used for markerless tracking" is not limited to the template T used for template matching. For example, when markerless tracking through machine learning is performed instead of template matching, an image input as input information to a model which has already learned machine learning corresponds to an example of "a reference image used for markerless tracking". In this case, an example of "a region in which the target position PT is determined by the target position identifier 140" corresponds to a region in which the target position PT is determined through machine learning.

The movement range of the target position PT is obtained in a planning stage for a therapeutic plan and is stored in the storage 160. The storage 160 stores information related to a margin applied to the movement range of the target position PT when the search region R is set. The search region setter 130 sets a part of a region of the fluoroscopic image TI as the search region R based on information related to the movement range of the target position PT and the margin stored in the storage 160. The set search region R can be manually changed. The method of setting the search region R disclosed here is an example. For example, various methods can be applied, such as manually inputting/setting a rectangular region by using the input/display 120, and causing the input/display 120 to display a plurality of candidates of the search region R and performing manual selection/setting. The method need only be able to suitably set the search region R and is not limited to those disclosed here.

<Corrector 131>

When an actual position of the imager 30 is deviated with respect to the reference position of the imager 30, there is a possibility that a DRR image obtained from three-dimensional volume data and the fluoroscopic image TI acquired from the imager 30 will not coincide with each other in detail. For example, the reference position of the imager 30 is a design position (the design position at which the radiation sources 12-1 and 12-2 and the detectors 13-1 and 13-2 are originally disposed) at which the imager 30 is originally disposed. For example, the state in which the actual position of the imager 30 is deviated indicates a case in which an installation error of the imager 30 with respect to a mounting place of the therapeutic device 10 (an installation error of the radiation sources 12-1 and 12-2 and the detectors 13-1 and 13-2) is present.

When the actual position of the imager 30 is deviated with respect to the reference position of the imager 30, the corrector 131 corrects the fluoroscopic image TI based on one or more correction values corresponding to a deviation amount of the imager 30 with respect to the reference position of the imager 30. That is, the corrector 131 corrects the fluoroscopic image TI to eliminate or reduce a difference generated between the DRR image and the fluoroscopic image TI due to a positional deviation of the imager 30. Hereinafter, this correction will be referred to as "alignment correction".

Here, the deviation amount of the imager 30 with respect to the reference position of the imager 30, or one or more correction values used for correcting the fluoroscopic image TI in accordance with the deviation amount are measured or calculated and are stored in the storage 160 in advance. For example, such a deviation amount or correction values can be obtained by comparing the fluoroscopic image TI obtained by the imager 30 performing imaging of a reference body having known dimensions, and a DRR image obtained from three-dimensional volume data in which the reference body is captured by the medical inspection device.

However, the reason that a DRR image and the fluoroscopic image TI do not coincide is not limited to the foregoing example. In place of an installation error of the imager 30, or in addition to an installation error of the imager 30, it may denote correction which can absorb the deviation amount other than the imager 30 (for example, a secular change in a building).

In the present embodiment, in a stage in which information processing in real time or close thereto is not necessary (for example, a preparation stage) among various therapy stages described below, the corrector 131 performs alignment correction with respect to the whole region of the fluoroscopic image TI acquired from the imager 30. On the other hand, in a stage in which information processing in real time or close thereto is necessary (for example, a checking stage and a therapy stage) among various therapy stages described below, the corrector 131 performs alignment correction with respect to only a part of the region of the fluoroscopic image TI acquired from the imager 30. That is, when information processing in real time or close thereto is necessary, the corrector 131 performs alignment correction with respect to an image of a predetermined region used for identifying the target position PT of the object P in the fluoroscopic image TI, and does not perform alignment correction with respect to an image of at least a part of the region out of a predetermined region in the fluoroscopic image TI. In the present embodiment, the predetermined region is the search region R in which the target position identifier 140 searches for the target position PT in the fluoroscopic image TI. From another viewpoint, the predetermined region is a region including the gating window and the periphery thereof.

That is, the predetermined region is a region larger than the outer shape of the gating window. The corrector 131 may correct a plurality of predetermined regions in the fluoroscopic image TI.

Figure 3:
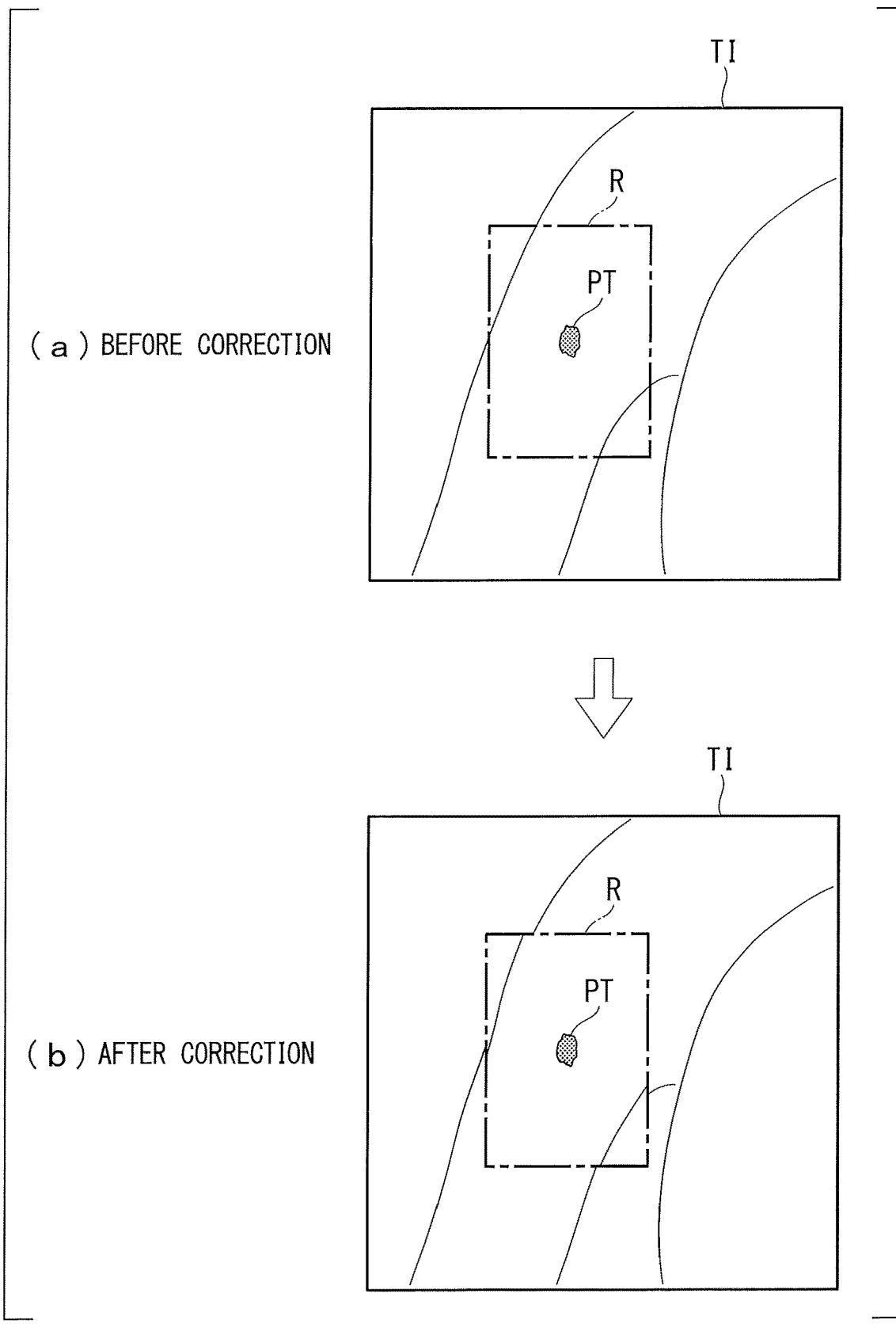
FIG. 3 is a view illustrating an example in which alignment correction is performed with respect to only the search region in the fluoroscopic image of the first embodiment.

FIG. 3 is a view illustrating an example in which the corrector 131 performs alignment correction with respect to only the search region R in the fluoroscopic image TI. In (a) of the diagrams, the fluoroscopic image TI before the corrector 131 performs alignment correction is illustrated. On the other hand, in (b) of the diagrams, the fluoroscopic image TI after the corrector 131 has performed alignment correction is illustrated. As illustrated in (b) of the diagram, when alignment correction is performed with respect to only a part of the region (the search region R) in the fluoroscopic image TI, a deviation like a step appears in a border between a region in which alignment correction is performed and a region in which alignment correction is not performed (a region outside the region in which alignment correction is performed).

<Display Controller 124>

The display controller 124 causes the input/display 120 to display a screen for displaying an image corrected by the corrector 131. In the present embodiment, the display controller 124 causes the gating window to be displayed in a manner of being superimposed on an image corrected by the corrector 131. The functions of the display controller 124 will be described below in detail.

<Flow of Therapy>

Hereinafter, a flow of a therapy in the therapy system 1 will be described. For example, the therapy system 1 is performed in a manner of being divided into a plurality of stages, such as a planning stage, a positioning stage, a preparation stage, a checking stage, and a therapy stage. For example, the therapy system 1 can perform a therapy by switching between three modes, such as markerless tracking and marker tracking which are internal respiratory synchronization, and external respiratory synchronization. Markerless tracking includes a technique of using a template matching method or machine learning. Hereinafter, markerless tracking using the template matching method will be described, and description will be given such that the gated irradiation method is employed as an irradiation method. The medical apparatus 100 may be switchable between the template matching method and a technique using machine learning.

[Planning Stage]

In the planning stage, first, CT imaging of the object P is performed. In CT imaging, images of the object P are captured in various directions for each of various respiratory phases. Next, 4D CT images are generated based on the results of the CT imaging. 4D CT images are n three-dimensional CT images (an example of the three-dimensional volume data described above) arranged in time series. A period obtained by multiplying this number n by the time interval between the time-series images is set to cover a period in which the respiratory phase changes by one cycle, for example. 4D CT images are stored in the storage 160.

Next, a physician, a radiologist, or the like inputs a contour with respect to one CT image of n CT images, for example. This contour is a contour of a tumor which is a lesion or a contour of an organ which is not intended to be irradiated with the therapeutic beam B. Next, for example, the image processor 136 sets the contour for each of n CT images through deformable registration. In this case, for example, the image processor 136 estimates movement of a lesion or an organ in n CT images based on the changes in positions of two or more characteristic elements included in each CT image, in n CT images, and deploys a contour of a lesion or an organ at a position reflecting the estimated movement of a lesion or an organ in n CT images.

Next, a therapeutic plan is decided. A therapeutic plan is a plan for regulating irradiation of the place, the direction, and the quantity of the therapeutic beam B in accordance with the position of a lesion based on information of the set contour. The therapeutic plan is decided in accordance with a therapeutic method such as the gated irradiation method or a tracking irradiation method. A part or all of the processing in the planning stage may be executed by an external device. For example, processing of generating 4D CT images may be executed by a CT device.

Here, a region defined by the contour of a tumor, the center of gravity in this region, the position of a characteristic spot of the object P, or the like becomes the target position PT. Moreover, in the therapeutic plan, the position which may be irradiated with the therapeutic beam B is decided as the target position PT. When the contour is set through deformable registration, a margin is automatically or manually set for the target position PT, and a gating window is set by applying the margin. This margin is provided to absorb an error in the device, positioning, and the like.

[Positioning Stage]

In the positioning stage, the bed position is adjusted. The object P is laid on the bed 11 and is fixed by using a shell or the like. First, the bed position is roughly adjusted. First, the bed position is roughly adjusted. In this stage, a worker visually checks for the position and the posture of the object P and moves the bed 11 to a position at which the object P will be irradiated with the therapeutic beam B from the irradiation gate 14. Accordingly, the position of the bed 11 is roughly adjusted. Next, an image to be utilized for minutely adjusting the bed position is captured. For example, when 3D-2D registration is performed, the fluoroscopic image TI is captured. For example, the fluoroscopic image TI is captured at the timing of the end of exhalation of the object P. Since the position of the bed 11 has already been roughly adjusted, an area near a target of the object P is imaged in the fluoroscopic image TI. For example, the fluoroscopic image TI is used after the corrector 131 performs alignment correction.

When 3D-2D registration is performed, in this stage, a DRR image is generated from three-dimensional volume data by using the radiation sources 12-1 and 12-2, the detectors 13-1 and 13-2, and the therapeutic plan information of the object P. The movement amount of the bed is calculated based on the DRR image and the fluoroscopic image TI, and the bed 11 is moved. The position of the bed 11 is minutely adjusted by repeating capturing the fluoroscopic image TI, correction by the corrector 131, calculating the movement amount of the bed, and moving the bed 11.

[Preparation Stage]

When the positioning stage ends, the processing shifts to the preparation stage. First, a DRR image of each phase is made from 4D CT images. The DRR image may be made at any time after the 4D CT images have been captured. In this case, a position, at which the gating window set in the therapeutic plan is projected, is set as the gating window on the DRR image. In the preparation stage, first, the fluoroscopic image TI which becomes a target to be selected as a reference image is captured. For example, the fluoroscopic image TI is captured such that two respirations of the object P are covered. The fluoroscopic image TI is subjected to alignment correction by the corrector 131. Hereinafter, the fluoroscopic image TI which has been subjected to alignment correction will also be simply referred to as "a fluoroscopic image TI". While the object P performs deep respirations, an external respiratory waveform of the object P is acquired by the sensor 15 synchronously with the fluoroscopic image TI. The display controller 124 causes the input/display 120 to display the acquired external respiratory waveform. A tracking value based on the respiratory phase of the object P obtained from the external respiratory waveform is associated with the captured fluoroscopic image TI.

In this stage, the relationship between the fluoroscopic image TI and the target position PT is learned from information of the DRR image and the target position on the DRR image. Moreover, correction of the target position PT by a physician is received. From the fluoroscopic image TI in which the target position PT has been learned, one or more templates T (reference images) are selected based on the tracking value. For example, the template T is obtained by cutting a part of the fluoroscopic image TI. The template T may be obtained by cutting a characteristic part of the fluoroscopic image TI. The template T may be obtained by performing predetermined processing, such as increasing the shades, with respect to an image cut out from the fluoroscopic image TI. Learning of the target position may be performed at any timing during a period from the planning stage to the therapy stage. For example, when the template T is made from the fluoroscopic image TI for one respiration of the first half of the fluoroscopic images TI for two respirations of the object P, whether a target can be tracked with the fluoroscopic image TI for one respiration of the second half may be checked by using the template T. In this case, the display controller 124 may cause the gating window set on the DRR image to be displayed on the fluoroscopic image TI.

[Checking Stage]

Capturing the fluoroscopic image TI is restarted. The target position identifier 140 performs matching of the template T with respect to the fluoroscopic images TI input in time series and allocates the target position PT with respect to the fluoroscopic image TI. While causing the input/display 120 to display the fluoroscopic images TI as a moving image, the display controller 124 causes the target position PT to be displayed in a manner of being superimposed on a frame of the fluoroscopic image TI in which the target position PT is allocated. As a result, the tracking results of the target position PT are checked by a physician or the like.

In this case, the display controller 124 causes the gating window set on the DRR image to be displayed on the fluoroscopic image TI. The output controller 150 determines whether or not the target position PT is settled within the gating window, regarding both the fluoroscopic images TI-1 and TI-2. In the therapy stage, a gate-on signal is output to the therapeutic device 10 when the target position PT is settled within the gating window. However, in the preparation stage, the presence or absence of an output of a gate-on signal is transmitted to the display controller 124 via the general controller 110. The display controller 124 causes the input/display 120 to display the presence or absence of an output of a gate-on signal in parallel with displaying of the moving image. As a result, the output timing of a gate-on signal is checked by a physician or the like.

[Therapy Stage]

In the therapy stage, the output controller 150 outputs a gate-on signal to the therapeutic device 10 when the target position PT is settled within the gating window, regarding both the fluoroscopic images TI-1 and TI-2. Accordingly, a therapy is performed by irradiating a lesion of the object P with the therapeutic beam B. In the case in which the target position PT is the position of a lesion, irradiation of the therapeutic beam B is performed when the tracked target position is settled within the gating window. In this case, the target is an example of "a predetermined target". In the case in which the target position PT is the position of a characteristic spot of the object P, irradiation of the therapeutic beam B is performed when the position of a lesion derived out from the target position PT is settled within the gating window, based on the relationship between the target position PT learned in advance and the position of a lesion. In this case, a lesion is an example of "a predetermined target". A portion at the position of a lesion may be irradiated with the therapeutic beam B by these complex techniques. That is, irradiation of the therapeutic beam B may be performed when a lesion is settled within a first gating window and a characteristic spot is settled within a second gating window, by setting each of the position of a lesion and the position of a characteristic spot as the target position.

<Display Image and Flowchart>

Hereinafter, processing of the medical apparatus 100 for supporting the flow of a therapy described above will be described.

Figure 4:
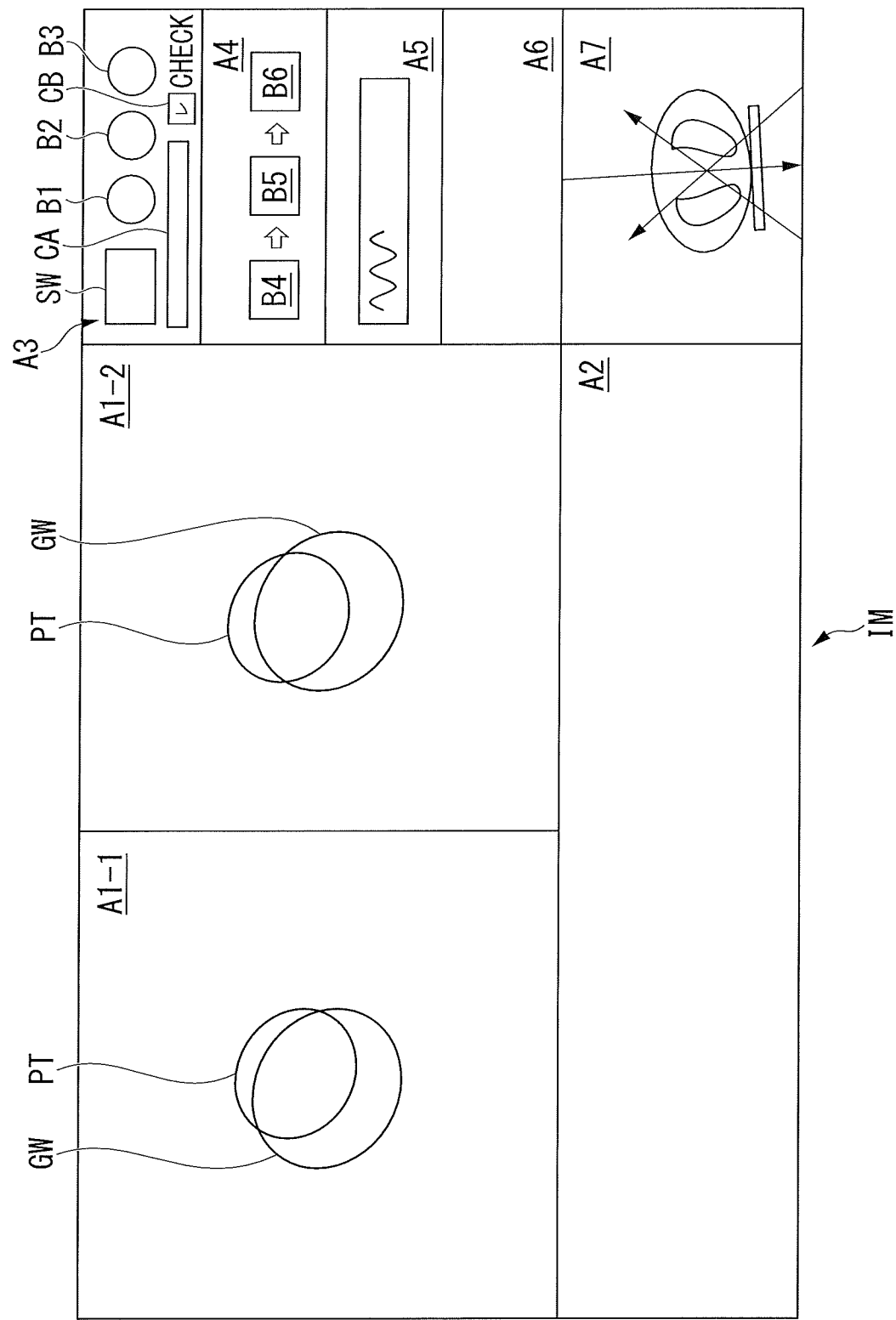
FIG. 4 is a view illustrating an example of an interface image displayed by an input/display of the medical apparatus of the first embodiment.

FIG. 4 is a view illustrating an example of an interface image IM which is displayed in the screen of the input/display 120 of the medical apparatus 100. For example, the interface image IM includes regions A1-1, A1-2, A2, A3, A4, A5, A6, and A7.

In the region A1-1, a gating window GW or a target position PT is displayed in a manner of being superimposed on the fluoroscopic image TI-1. In the region A1-2, the gating window GW or the target position PT is displayed in a manner of being superimposed on the fluoroscopic image TI-2. In the region A2, various graphs and the like are displayed. For example, the fluoroscopic images TI displayed in A1-1 and A1-2 are images in the search region R subjected to alignment correction by the corrector 131.

Figure 5:
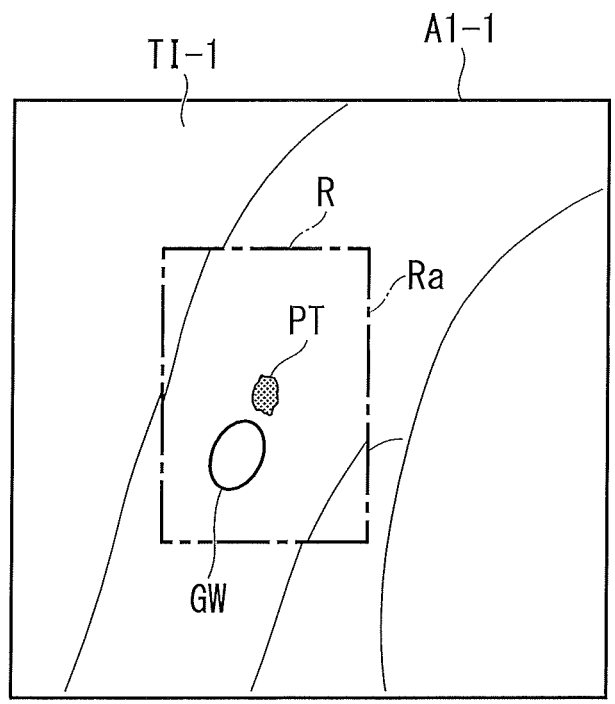
FIG. 5 is a view illustrating an example of a fluoroscopic image displayed in a region of the first embodiment.

FIG. 5 is a view illustrating an example of the fluoroscopic image TI-1 displayed in a region A1-1. The display controller 124 causes the fluoroscopic image TI-1 which is an image in the search region R subjected to alignment correction by the corrector 131 to be displayed in the region A1-1 of the input/display 120. In this case, the display controller 124 causes the gating window GW and the target position PT to be displayed in a manner of being superimposed on an image of the search region R subjected to alignment correction by the corrector 131.

In the present embodiment, the display controller 124 causes an image acquired by the acquirer 128 (an image which is not subjected to alignment correction) to be displayed in a region corresponding to the outer side of the search region R in the region A1-1. Accordingly, a physician or the like can also check for the state of the region outer side the search region R. In this case, as described above, a deviation like a step appears in a border between a region in which alignment correction is performed (the search region R) and a region in which alignment correction is not performed (a region outside the search region R). A physician, a radiologist, or the like can check that alignment correction is reliably performed with respect to the search region R by checking for this deviation like a step. In this case, a line Ra indicating the outer edge (the outer shape) of the search region R may be displayed in the fluoroscopic image TI.

When alignment correction is performed with respect to an image of the search region R in the fluoroscopic image TI and an image subjected to alignment correction is displayed in a region corresponding to the search region R before being corrected, in the screen of the input/display 120, there are cases in which a blank is generated within the search region R in the screen. For example, there are cases in which a blank is generated between an image of the search region R corrected by the corrector 131 and an uncorrected image displayed to correspond to the outer side of the search region R. In this case, the display controller 124 may perform any of the following processing (1) to (3).

(1) The display controller 124 obtains a correspondence relationship between image coordinates of an image of the search region R before correction is performed by the corrector 131 and image coordinates of an image of the search region R after correction is performed by the corrector 131, based on one or more correction values used by the corrector 131, and causes an image of the search region R after being corrected to be displayed without a blank with respect to an uncorrected image displayed to correspond to an area out of the search region R in the screen. That is, when the image coordinates of an image before alignment correction are (u, v), and the image coordinates after alignment correction are (x, y), the following relationships are established.

$$x = au + bv$$

$$y = cu + dv$$

Here, a, b, c, d are values obtained based on correction values of the alignment correction. That is, the image coordinates before alignment correction can correspond to all of the image coordinates after alignment correction by suitably setting the foregoing coefficients (a, b, c, and d). Therefore, the region corresponding to the search region R before alignment correction in the screen can be filled with an image after alignment correction by performing additional image processing (for example, in a case of copy or decimal pixels, the average or the like) as necessary. Accordingly, a blank can be prevented from being generated in the screen.

Here, when the pixels before alignment correction protrude from the region corresponding to the search region R, a warning may be issued by the input/display 120 or a notifier 126 such that a user changes the search region R, the search region R may be automatically changed, or calculation of a portion protruding from the region corresponding to the search region R may be omitted.

(2) The corrector 131 corrects a region larger than the search region R in the fluoroscopic image TI. The display controller 124 causes an image corrected by the corrector 131 to be displayed without a blank with respect to an uncorrected image displayed to correspond to an area out of the search region R in the screen. That is, the corrector 131 corrects a region larger than the search region R (for example, a region larger than the search region R by x [mm] set in advance). An image subjected to alignment correction is displayed in the whole area of the region corresponding to the search region R before alignment correction in the screen. Accordingly, a blank can be prevented from being generated in the screen.

(3) The display controller 124 displays a blank between an image corrected by the corrector 131 and an uncorrected image displayed to correspond to an area out of a predetermined region in the screen, or displays an uncorrected image. In these cases, a warning may be output by the input/display 120 or the notifier 126.

In the example illustrated in FIG. 5, when the line Ra indicating the outer edge of the search region R before correction is displayed in the fluoroscopic image TI, the expression "without a blank with respect to an uncorrected image displayed to correspond to an area out of the search region R in the screen (or, with a blank, or displays an uncorrected image)" in the foregoing description of (1) to (3) may denote that "without a blank with respect to the line Ra indicating the outer edge of the search region R before correction (or, with a blank, or displays an uncorrected image)".

Figure 6:
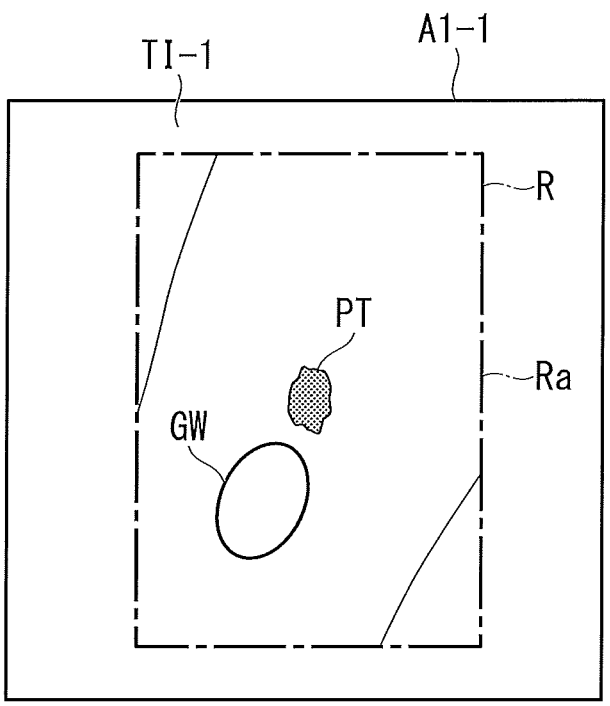
FIG. 6 is a view illustrating another example of a fluoroscopic image displayed in the region of the first embodiment.

On the other hand, FIG. 6 is a view illustrating another example of the fluoroscopic image TI-1 displayed in the region A1-1. The display controller 124 does not have to cause an image acquired by the acquirer 128 to be displayed in the region corresponding to the outer side of the search region R in the region A1-1. In this case, in the region A1-1, for example, an image of the search region R may be displayed in an enlarged manner. According to such a configuration, an image having no deviation can be displayed for a user feeling uncomfortable with the deviation like a step provided in the border portion between the inner side and the outer side of the search region R in the fluoroscopic image TI-1. In this case, the line Ra indicating the outer edge (the outer shape) of the search region R may be displayed in the fluoroscopic image TI.

In the example illustrated in FIG. 6 as well, when alignment correction is performed with respect to an image of the search region R in the fluoroscopic image TI, and an image subjected to alignment correction is displayed in the region corresponding to the search region R before correction in the screen of the input/display 120, there are cases in which a blank will be generated within the search region R in the screen. In the case of the example illustrated in FIG. 6, there are cases in which a blank is generated between an image of the search region R corrected by the corrector 131 and the line Ra indicating the outer edge of the search region R before correction. Therefore, even in the example illustrated in FIG. 6, the display controller 124 may perform any of the foregoing processing (1) to (3). In this case, the expression "without a blank with respect to an uncorrected image displayed to correspond to an area out of the search region R in the screen (or, with a blank, or displays an uncorrected image)" in the foregoing description of (1) to (3) is interpreted as "without a blank with respect to the line Ra indicating the outer edge of the search region R before correction (or, with a blank, or displays an uncorrected image)".

Referring back to FIG. 4, in the region A3, a selection window SW for receiving selection of a mode and the like, a first button B1 for instructing the therapeutic device 10 to start capturing or stop capturing the fluoroscopic image TI, a second button B2 for instructing the therapeutic device 10 to temporarily stop capturing the fluoroscopic image TI, a third button B3 for instructing the therapeutic device 10 to end a therapeutic session, a slide bar for tracing back and checking for the fluoroscopic images TI in time series, a control area CA in which a frame advancing switch and the like are set, a check box CB for checking for completion of the checking stage, and the like are set. For example, an operation with respect to each part of the interface image IM is performed by performing a touching operation, clicking a mouse, operating a keyboard, or the like. For example, the first button B1 is operated by performing a touching operation or clicking a mouse.

In the region A4, a fourth button B4, a fifth button B5, and a sixth button B6 for instructing the therapeutic device 10 that the therapy stage corresponding to the mode proceeds to a next step are set. In the region A5, the graph of the external respiratory waveform based on the output value of the sensor 15, and the like are displayed. In the region A6, an image indicating the therapeutic plan information of the object P, and text information are displayed. In the region A7, the irradiation direction of an X-ray, the irradiation field, the irradiation direction of the therapeutic beam B, the contour of a target, the marker region of interest (ROI), and the like are displayed in a manner of being superimposed on a cross section of a CT image of the object P.

Figure 7:
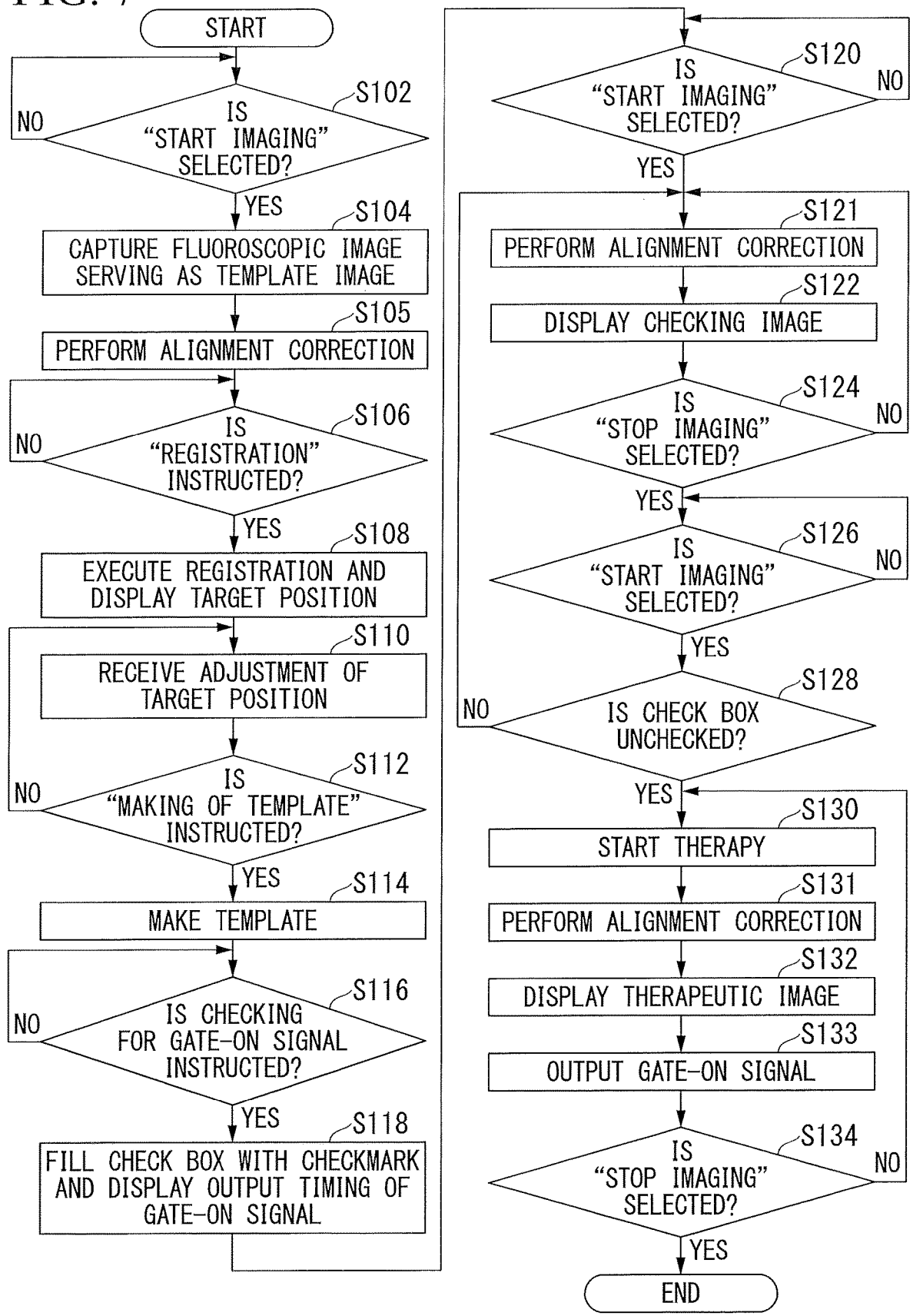
FIG. 7 is a flowchart (Part 1) illustrating an example of a flow of processing executed by the medical apparatus of the first embodiment.

Hereinafter, various functions of the interface image IM will be described with reference to the flowchart. FIG. 7 is a flowchart (Part 1) illustrating an example of a flow of processing executed by the medical apparatus 100. In the following description, when it is detected that an operation has been performed with respect to the medical apparatus 100, the general controller 110 is regarded to perform determination with reference to the information input from the input operation acquirer 122, and description for each case will be omitted. Here, description will be given on the premise that markerless tracking has been selected.

Figure 8:
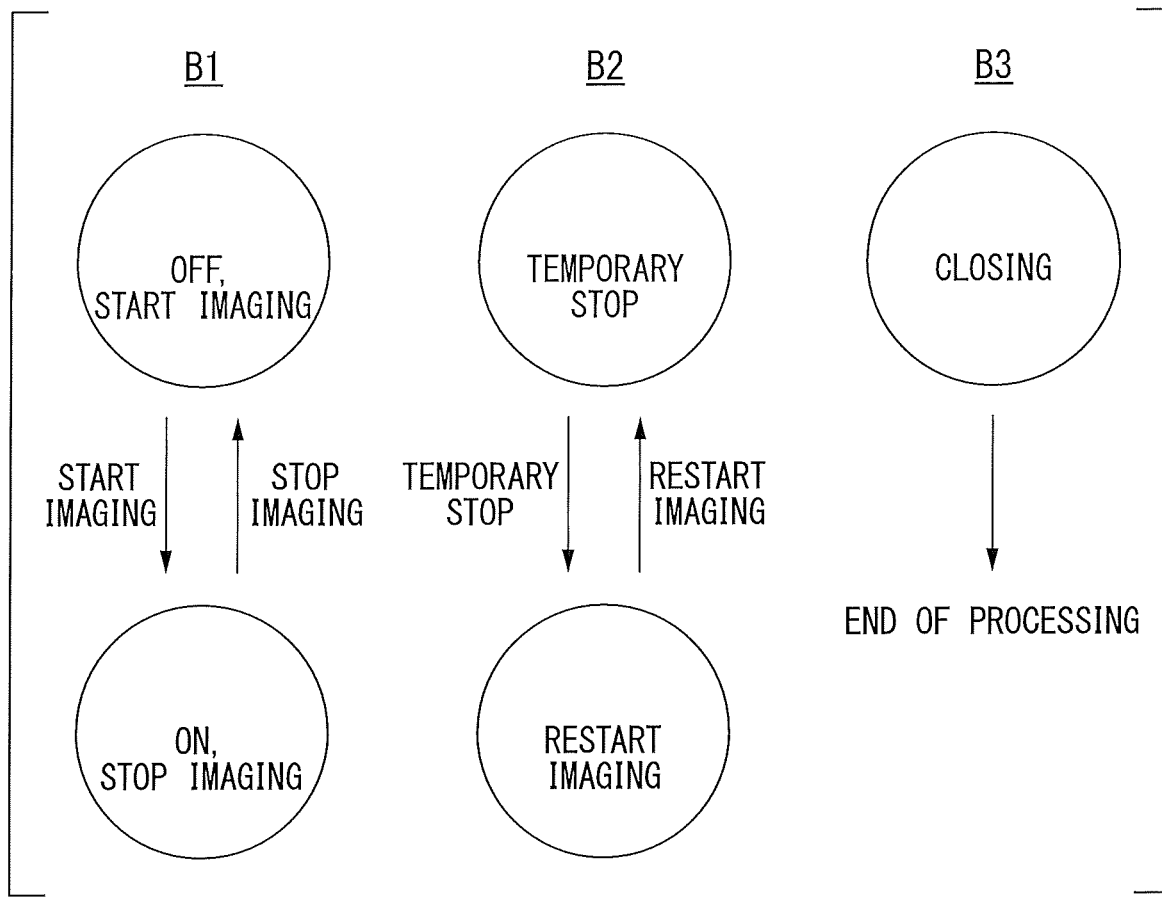
FIG. 8 is a view illustrating a change in a form of displaying a first button, a second button, and a third button of the first embodiment.

First, the general controller 110 determines whether or not start imaging is selected by operating the first button B1 (Step S102). FIG. 8 is a view illustrating a change in a form of displaying the first button B1, the second button B2, and the third button B3. As illustrated in the diagram, in an initial state, the first button B1 indicates a state in which imaging is "OFF", that is, stopped in a form of receiving an instruction for "start imaging". When the first button B1 is operated, a state in which imaging is "ON", that is, executed is indicated, and the first button B1 changes into a form of receiving an instruction for "stop imaging". The first button B1 performs state transition between these two forms.

In an initial state, the second button B2 is in a form of receiving an instruction for "temporary stop" of imaging when being operated. When being operated, the second button B2 changes into a form of receiving an instruction for "restart imaging". In an initial state, the third button B3 is in a form of receiving an instruction for "closing" of the interface image IM. When the third button B3 is operated, the interface image IM is stopped being displayed, and a series of processing ends.

When start imaging is selected by operating the first button B1, the general controller 110 instructs the output controller 150 to instruct the therapeutic device 10 to capture the fluoroscopic image TI which becomes a template image (Step S104). For example, the output controller 150 instructs the therapeutic device 10 to capture the fluoroscopic images TI for k times of respirations. The output controller 150 may output an instruction for ending imaging to the therapeutic device 10 when the first button B1 is operated again. In this manner, the output controller 150 outputs an instruction for an operation to the imager (the radiation sources 12-1 and 12-2, and the detectors 13-1 and 13-2) of the therapeutic device 10 in accordance with the details of the input operation acquired by the input operation acquirer 122. Accordingly, the medical apparatus 100 can manage an operation of the therapy system 1 including the therapeutic device 10 in an integrated manner, so that convenience is improved.

Next, the corrector 131 performs alignment correction with respect to the fluoroscopic image TI (Step 105). In this Step 105, alignment correction may be performed with respect to the whole region of the fluoroscopic image TI, or alignment correction may be performed with respect to only a part of the region of the fluoroscopic image TI. For example, when the search region R is not set yet with respect to the fluoroscopic image TI, the corrector 131 performs alignment correction with respect to the whole region of the fluoroscopic image TI.

Figure 9:
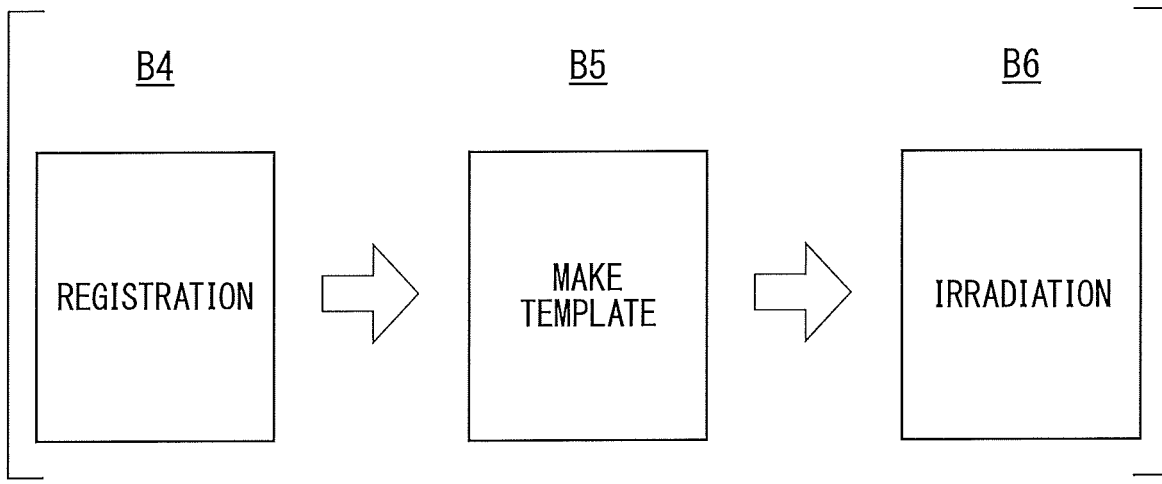
FIG. 9 is a view illustrating details of a fourth button, a fifth button, and a sixth button of the first embodiment.
Figure 10:
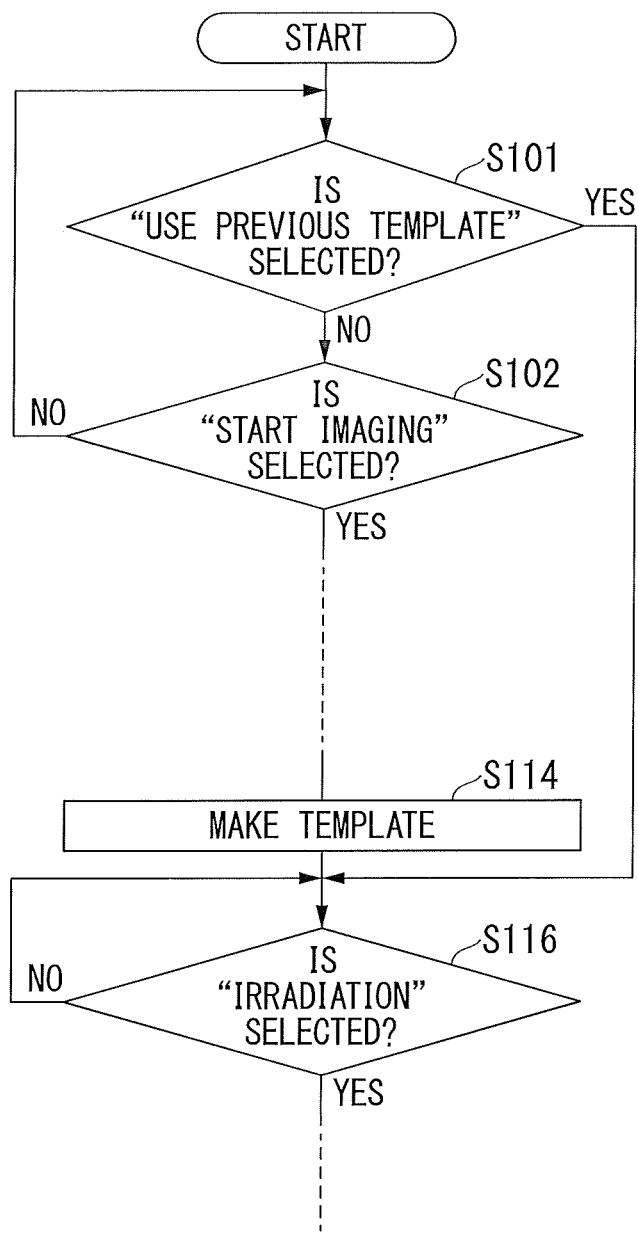
FIG. 10 is a flowchart (Part 2) illustrating an example of a flow of processing executed by the medical apparatus of the first embodiment.

Next, the general controller 110 determines whether or not registration is instructed by operating the fourth button B4 (Step S106). "Registration" denotes an operation of associating the target position PT with a template image. FIG. 9 is a view illustrating details of the fourth button B4, the fifth button B5, and the sixth button B6. The fourth button B4 receives an instruction for registration, the fifth button B5 receives an instruction for making a template, and the sixth button B6 receives an instruction for irradiation.

When registration is instructed by operating the fourth button B4, the general controller 110 instructs the image processor 136 to obtain a target position in the fluoroscopic image TI from the target position PT in a DRR image, and instructs the display controller 124 to cause the input/display 120 to display the obtained target position PT in a manner of being superimposed on the fluoroscopic image TI (Step S108). As described above, the image processor 136 performs processing of matching characteristic portions in images between the DRR image of which the target position PT is already known and the fluoroscopic image TI, based on the DRR image made from a CT image captured in the planning stage, or the fluoroscopic image TI captured after the planning stage, thereby deriving out the target position PT in the fluoroscopic image TI. The relationship between the fluoroscopic image TI and the target position PT is provided for the reference image maker 132. An image in which the target position PT is superimposed on the fluoroscopic image TI is displayed in the regions A1-1 and A1-2 of the interface image IM, for example. In this state, the general controller 110 receives an adjustment of the target position PT (Step S110). For example, the target position PT is adjusted by performing a drag/drop operation with respect to the regions A1-1 and A1-2. When the target position PT is adjusted, the general controller 110 provides the adjusted relationship between the fluoroscopic image TI and the target position PT for the reference image maker 132.

Next, the general controller 110 determines whether or not making a template is instructed by operating the fifth button B5 (Step S112). When making a template is instructed by operating the fifth button B5, the general controller 110 instructs the reference image maker 132 to select the fluoroscopic image TI to be used for generating the template T, for example, the template T is generated by cutting out a part of the fluoroscopic image TI (Step S114). The reference image maker 132 makes the template T with which the target position PT is associated and causes the storage 160 to store the template T.

Next, the general controller 110 determines whether or not checking for a gate-on signal is instructed by operating the sixth button B6 (Step S116). When checking for a gate-on signal is instructed, the general controller 110 instructs the display controller 124 to change the check box CB into a state filled with checkmark (check). (Step S118). In the state in which the check box CB is filled with checkmark, the output timing of a gate-on signal is calculated and displayed, but a gate-on signal is not actually output to the therapeutic device 10.

Next, the general controller 110 determines whether or not start imaging is selected by operating the first button B1 (Step S120). When start imaging is selected by operating the first button B1, the general controller 110 instructs the output controller 150 to instruct the therapeutic device 10 to capture the fluoroscopic image TI. The general controller 110 instructs the corrector 131 to perform alignment correction with respect to the fluoroscopic image TI acquired by the acquirer 128 from the therapeutic device 10 (Step S121). In this Step 121, the corrector 131 performs alignment correction with respect to only the search region R of the fluoroscopic image TI. Moreover, the general controller 110 causes the display controller 124 to instruct the input/display 120 to display the checking image obtained by performing alignment correction with respect to search region R of the fluoroscopic image TI (Step S122).

The checking image is displayed in the regions A1-1 and A1-2. The checking image is an image in which the target position PT or the gating window GW is superimposed on the fluoroscopic image TI which is reproduced as a moving image (refer to FIG. 2). The output controller 150 outputs a gate-on signal to the display controller 124, which displays the gate-on signal in the region A2 when the target position PT (predetermined target) is settled in the gating window GW. A physician or the like can check for whether or not the target position PT such as a lesion of the object P is recognized as a correct position, whether or not the timing the target position PT is settled in the gating window GW is appropriate, the output efficiency of a gate-on signal, and the like, by visually recognizing this checking image. The checking image is displayed until stop imaging is selected by operating the first button B1 (Step S124). Even after stop imaging is selected, the checking image can be traced back and checked for by operating the control area CA in which the slide bar, the frame advancing switch, and the like are set.

When stop imaging is selected by operating the first button B1, the general controller 110 determines whether or not start imaging is selected by operating the first button B1 (Step S126). The general controller 110 may start imaging when the medical apparatus 100 receives a start signal from the therapeutic device 10. When start imaging is selected by operating the first button B1, the general controller 110 determines whether or not checkmark of the check box CB is canceled (Step S128). When checkmark of the check box CB is not canceled, processing from Step S121 to Step S126 is performed again. When checkmark of the check box CB is canceled, the general controller 110 instructs the display controller 124, the target position identifier 140 and the output controller 150 to start a therapy, and the output controller 150 instructs the therapeutic device 10 to capture the fluoroscopic image TI (Step S130). In the processing in Step 128, when the check box CB is not unchecked but the check box CB is unchecked in the middle of imaging, the general controller 110 may cause the output controller 150 to output a gate-on signal at that timing (not illustrated). In this manner, in the interface image IM, the output controller 150 outputs a gate-on signal to the therapeutic device 10 on condition that an input operation of causing a default state to be a cancel state is acquired by the input operation acquirer 122. Accordingly, unintentional irradiation of the therapeutic beam B to the object P is suppressed, and reliability of a therapy can be enhanced. When making a template is completed, without requiring an ending operation of the preparation stage and the checking stage, the input operation acquirer 122 receives an instruction to start the irradiation stage of the therapeutic beam B. Accordingly, it is possible to improve operability of the medical apparatus 100.

When a therapy starts, the general controller 110 instructs the output controller 150 to instruct the therapeutic device 10 to capture the fluoroscopic image TI. The general controller 110 instructs the corrector 131 to perform alignment correction with respect to the fluoroscopic image TI acquired by the acquirer 128 from the therapeutic device 10 (Step S131). In this Step 131, the corrector 131 performs alignment correction with respect to only the search region R of the fluoroscopic image TI. Moreover, the general controller 110 instructs the display controller 124 to cause the input/display 120 to display a therapeutic image obtained by performing alignment correction with respect to only the search region R of the fluoroscopic image TI (Step S132). A therapeutic image is displayed in the regions A1-1 and A1-2.

The target position identifier 140 performs matching of the fluoroscopic image TI and the template T and identifies the target position PT based on the position of the fluoroscopic image with which the template T coincides.

The output controller 150 outputs a gate-on signal to the therapeutic device 10 when the target position PT (predetermined target) is settled within the gating window GW (Step S133). A therapy continues until stop imaging is selected by operating the first button B1 (Step S134). The medical apparatus 100 may end a therapy even when a signal of completing irradiation is received from the therapeutic device 10 or when a signal indicating that an operation of ending irradiation is conducted in the therapeutic device 10 is received from the therapeutic device 10. In this manner, the output controller 150 outputs an instruction for an operation to the imager (the radiation sources 12-1 and 12-2, and the detectors 13-1 and 13-2) of the therapeutic device 10, and a particular function (the target position identifier 140 or the like) of the medical apparatus 100 is activated in accordance with a unit-based input operation (an operation of the first button B1) acquired by the input operation acquirer 122. Accordingly, the medical apparatus 100 can manage an operation of the therapy system 1 including the therapeutic device 10 in an integrated manner, so that convenience is improved.

The display controller 124 may change the color (for example, the color of the border line indicating the outer shape of the gating window GW) of the gating window GW when a gate-on signal is output (in the checking stage, when the conditions for outputting a gate-on signal are fulfilled) in the checking image and the therapeutic image.

For example, regarding both the fluoroscopic images TI-1 and TI-2, the border line of the gating window GW may be displayed in a first color when the target position PT (predetermined target) is not settled in the gating window GW, may be displayed in a second color when the target position PT is settled in the gating window GW in only one of both the fluoroscopic images TI-1 and TI-2, and may be displayed in a third color when the target position PT is settled in the gating window GW (that is, when the conditions for outputting a gate-on signal are fulfilled) in both the fluoroscopic images TI-1 and TI-2. An error icon may be displayed when the target position PT is not settled in the gating window GW in both the fluoroscopic images TI-1 and TI-2.

When the conditions for outputting a gate-on signal are fulfilled, the display controller 124 may change the hue or the brightness of any of an inner region or an outer region of the gating window GW. Moreover, the medical apparatus 100 may include a notifier 126 that issues notification by a sound or a vibration when the conditions for outputting a gate-on signal are fulfilled.

The mode switching between markerless tracking, marker tracking, and external respiratory synchronization may be received at an arbitrary timing during a period from the preparation stage to the therapy stage, instead of being received in the therapy stage. Suitably, redoing of the processing is received. For example, in a scene displaying the checking image, an operation for redoing the processing from the step of imaging a reference image is received. When the mode switching is performed after the fluoroscopic image TI is captured, the fluoroscopic image TI which has already been captured may be employed as a template.

When a therapy is performed in a divided manner over a plurality of times, the therapy may be performed by succeeding a template T made before a previous therapy. FIG. 7 is a flowchart (Part 2) illustrating an example of a flow of processing executed by the medical apparatus 100. As illustrated in the diagram, after markerless tracking is selected in the selection window SW, the general controller 110 determines whether or not "use previous template" is selected in any of the regions (Step S101). When "use previous template" is selected, the processing skips Steps S102 to S114, and the processing proceeds to Step S116. Accordingly, convenience is improved, and reliability of a therapy is improved.

According to the configuration as described above, it is possible to provide the medical apparatus 100 which can grasp the position of a target of the object P without a significant delay in time even when the fluoroscopic image TI needs to be corrected. That is, when positional deviation or the like of the imager 30 is present, the corrector 131 of the medical apparatus 100 according to the present embodiment corrects an image of a predetermined region including the target position PT of the object P in the fluoroscopic image TI but does not correct an image of at least a part of the region out of the predetermined region in the fluoroscopic image TI. According to such a configuration, the processing time required for correction can be shortened compared to a case of correcting the fluoroscopic image TI in its entirety. Accordingly, even when the fluoroscopic image TI needs to be corrected, the position of a target of the object P can be grasped without a significant delay.

In the present embodiment, the predetermined region is the search region R in which the target position identifier 140 searches for the target position PT in the fluoroscopic image TI. According to such a configuration, a region to be corrected by the corrector 131 is limited to the search region R. Accordingly, the time required for correction of the fluoroscopic image TI can be further shortened.

In the present embodiment, the display controller 124 of the medical apparatus 100 causes the input/display 120 to display a screen for displaying an image TI corrected by the corrector 131. According to such a configuration, the input/display 120 can display the fluoroscopic image TI corrected in real time. Accordingly, a physician or the like can check for the corrected fluoroscopic image TI without a significant delay in time.

In the present embodiment, the display controller 124 causes the uncorrected fluoroscopic image TI acquired by the acquirer 128 to be displayed in a region corresponding to an area out of the predetermined region in the screen. According to such a configuration, a physician or the like can check for the corrected fluoroscopic image TI regarding the predetermined region and can also grasp an approximate state of regions other than the predetermined region in parallel.

In the present embodiment, the display controller 124 does not cause the fluoroscopic image TI acquired by the acquirer 128 to be displayed in a region corresponding to an area out of the predetermined region in the screen. According to such a configuration, it is possible to avoid displaying an image having a deviation like a step in the border between the predetermined region and its outer region.

Second Embodiment

Next, a medical apparatus 100A according to the second embodiment will be described. The present embodiment differs from the first embodiment in the fact that the reference image maker 132A has a learner 132a. However, configurations other than described below are substantially the same as the medical apparatus 100 according to the first embodiment.

Figure 11:
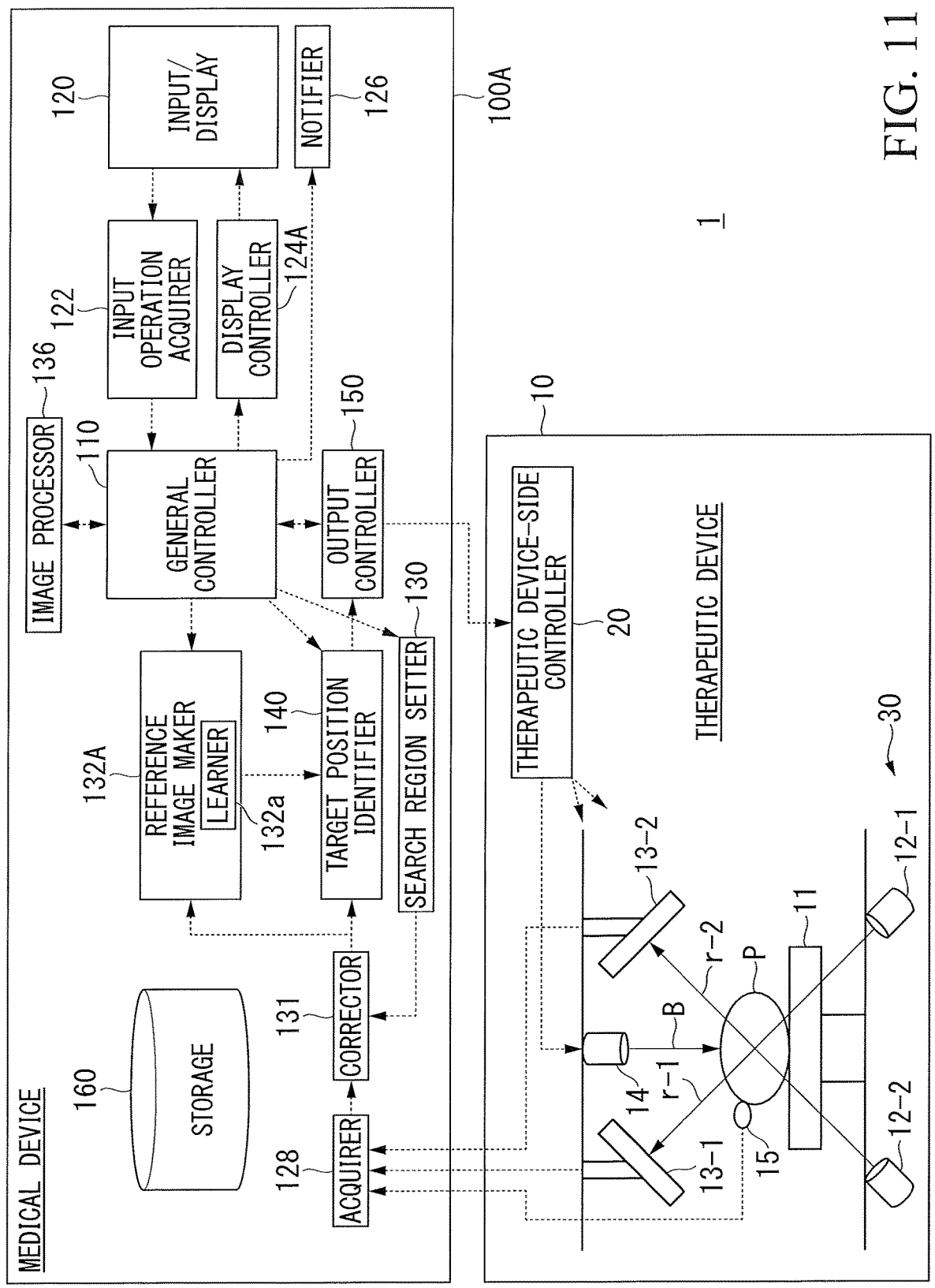
FIG. 11 is a configuration diagram of a therapy system including a medical apparatus according to a second embodiment.

FIG. 11 is a configuration diagram of the therapy system 1 including the medical apparatus 100A according to the second embodiment.

For example, the therapy system 1 includes the therapeutic device 10 and the medical apparatus 100A. The medical apparatus 100A has the reference image maker 132A in place of the reference image maker 132 of the first embodiment. The basic function of the reference image maker 132A is similar to that of the reference image maker 132.

In the present embodiment, the reference image maker 132A has the learner 132a. When a therapy is divided into a plurality of times (a plurality of days), the learner 132a learns a pattern (for example, a pattern having a shape of the target appears in the fluoroscopic image TI) of the target based on a plurality of DRR images obtained from three-dimensional volume data (for example, 4D CT images) in the first therapy, and generates a reference image used for markerless tracking. For example, the learner 132a generates the template T for tracking the target through template matching. The pattern of the target is an example of "information related to the target". In the second therapy and thereafter, the learner 132a learns the pattern of the target based on a plurality of fluoroscopic images TI acquired by the acquirer 128 at the time of the preceding therapy and regenerates the template T. Accordingly, the target can be tracked by using the template T reflecting a chronological change in the body of the object P, so that accuracy of the target tracking can be enhanced. A template having high reliability may be automatically or manually selected based on a comparison between tendencies of the position, movement, and the like of a target on the day of the therapy. Accordingly, even in a therapy performed a plurality of times, it is possible to select a template in which the target position on the day of the therapy can be accurately identified, so that it is no longer necessary to capture a fluoroscopic image for making a new template. In the present embodiment, the fluoroscopic image TI used for learning the pattern of the target is an image subjected to alignment correction by the corrector 131.

Figure 12:
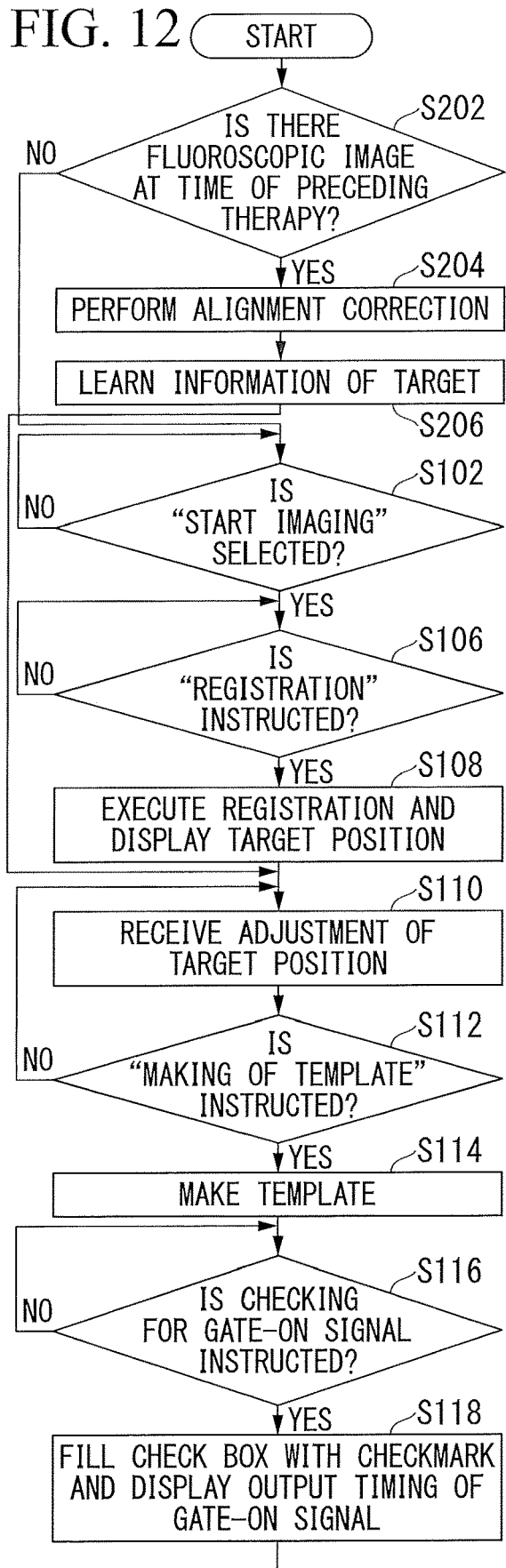
FIG. 12 is a flowchart illustrating an example of a flow of processing executed by the medical apparatus of the second embodiment.
Figure 12:
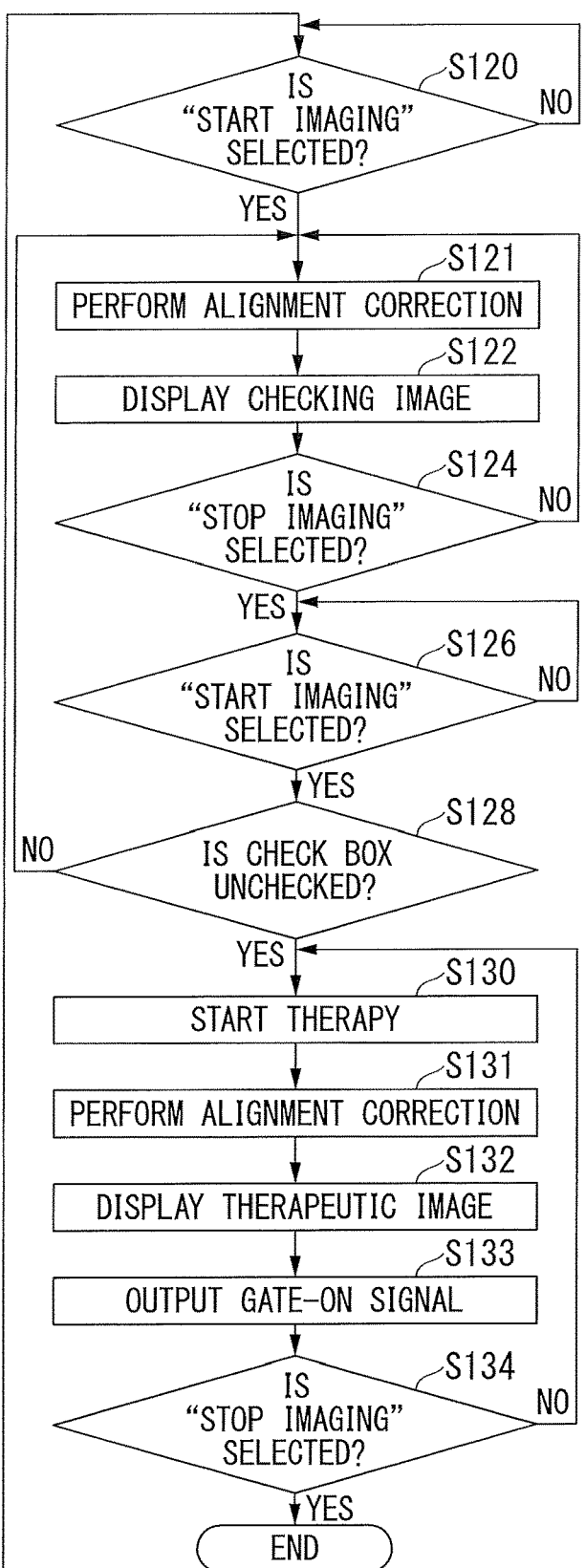

FIG. 12 is a flowchart illustrating an example of a flow of processing executed by the medical apparatus 100A. Here, a case of markerless tracking will be described. First, when the therapy is a second therapy or thereafter, the general controller 110 determines whether or not there is the fluoroscopic image TI which has been acquired by the acquirer 128 at the time of the preceding therapy and has been stored in the storage 160 (Step S202). When the fluoroscopic image TI at the time of the preceding therapy is present, the general controller 110 causes the corrector 131 to perform alignment correction with respect to the fluoroscopic image TI (Step S204). The reference image maker 132A learns the pattern of the target based on the fluoroscopic image TI subjected to alignment correction by the corrector 131 (Step S206). The reference image maker 132A generates the template T based on the pattern of the learned target. In this case, processing from Step S102 to S106 is omitted, and the processing of Step S110 is performed.

On the other hand, when the fluoroscopic image TI at the time of the preceding therapy is not present, the general controller 110 may generate the template T based on a DDR image obtained from 4D CT images. Alternatively, the general controller 110 may acquire the fluoroscopic image TI which will serve as a template image by the imager 30 and the acquirer 128 and to generate the template T based on the acquired fluoroscopic image TI.

Hereinabove, several embodiments have been described. However, the embodiments are not limited to the foregoing examples. For example, when markerless tracking through machine learning is performed, only an image (calculation region) cut out from the fluoroscopic image TI and input to a model which has already learned machine learning may be corrected. One or a plurality of images (calculation regions) input to a model which has already learned may be corrected.

The foregoing embodiment can be expressed as follows.

A medical apparatus is configured to include a hardware processor, and a storage device that stores a program.

The hardware processor executes the program to acquire a fluoroscopic image of an object from an imager which performs imaging by irradiating the object with an electromagnetic wave to generate the fluoroscopic image, to correct an image of one or more predetermined regions used for identifying a target position of the object in the fluoroscopic image based on one or more correction values but does not correct an image of at least a part of a region out of the predetermined region in the fluoroscopic image, to identify the target position based on the corrected image, and to output an irradiation permission signal to a therapeutic device which irradiates the object with a therapeutic beam based on the identified target position.

According to at least one of the embodiments described above, the corrector of the medical apparatus corrects an image of a predetermined region including the target position of the object in the fluoroscopic image based on one or more correction values but does not correct an image of at least a part of a region out of the predetermined region in the fluoroscopic image. According to such a configuration, it is possible to grasp a position of a target of an object without a significant delay even when a fluoroscopic image needs to be corrected.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical apparatus comprising:
    an acquirer configured to acquire a fluoroscopic image of an object from an imager which performs imaging by irradiating the object with an electromagnetic wave to generate a fluoroscopic image;
    a corrector configured to correct an image of one or more predetermined regions used for identifying a target position of the object in the fluoroscopic image based on one or more correction values but does not correct an image of at least a part of a region out of the predetermined region in the fluoroscopic image;
    an identifier configured to identify the target position based on an image corrected by the corrector;
    an output controller configured to output an irradiation permission signal to a therapeutic device which irradiates the object with a therapeutic beam based on the target position identified by the identifier; and
    a search region setter configured to set a search region with respect to the fluoroscopic image acquired by the acquirer,
    wherein the corrector is configured to correct an image of the search region set by the search region setter but does not correct an image of a region out of the search region in the fluoroscopic image.

2. The medical apparatus according to claim 1, wherein the predetermined region is a region including the target position in the fluoroscopic image.

3. The medical apparatus according to claim 1,
wherein the output controller is configured to output the irradiation permission signal when a predetermined target is settled in a irradiation permission range, and
wherein the predetermined region is a region larger than the irradiation permission range.

4. The medical apparatus according to claim 1, wherein the correction value is provided based on an installation error of the imager.

5. The medical apparatus according to claim 1, further comprising:
a display controller configured to cause a display to display a screen for displaying an image corrected by the corrector.

6. The medical apparatus according to claim 5,
wherein the output controller is configured to output the irradiation permission signal when a predetermined target is settled in a irradiation permission range, and
wherein the display controller is configured to cause the irradiation permission range to be displayed in a manner of being superimposed on an image corrected by the corrector.

7. The medical apparatus according to claim 5, wherein the display controller is configured to cause an uncorrected fluoroscopic image acquired by the acquirer to be displayed in a region corresponding to an area out of the predetermined region in the screen.

8. The medical apparatus according to claim 5, wherein the display controller is configured to restrain a fluoroscopic image acquired by the acquirer from being displayed in a region corresponding to an area out of the predetermined region in the screen.

9. The medical apparatus according to claim 7, wherein the display controller is configured to obtain a correspondence relationship between image coordinates of an image of the predetermined region before correction is performed by the corrector and image coordinates of an image of the predetermined region after correction is performed by the corrector, based on the one or more correction values, and cause an image of the predetermined region after being corrected to be displayed without a blank with respect to an uncorrected image displayed to correspond to an area out of the predetermined region in the screen, or a line corresponding to an outer edge of the predetermined region before being corrected in the image.

10. The medical apparatus according to claim 7,
wherein the corrector is configured to correct a region larger than the predetermined region in the fluoroscopic image, and
wherein the display controller is configured to cause an image corrected by the corrector to be displayed without a blank with respect to an uncorrected image displayed to correspond to an area out of the predetermined region in the screen, or a line corresponding to an outer edge of the predetermined region before being corrected in the image.

11. The medical apparatus according to claim 7, wherein the display controller is configured to display a blank between an image corrected by the corrector and an uncorrected image displayed to correspond to an area out of the predetermined region in the screen or a line corresponding to an outer edge of the predetermined region before being corrected in the image, or display an uncorrected image.

12. The medical apparatus according to claim 1, further comprising:

a learner configured to perform learning regarding a target of the object based on an image corrected by the corrector,
wherein the identifier is configured to identify the target position based on information regarding the target learned by the learner.

13. The medical apparatus according to claim 5,
wherein the output controller is configured to output the irradiation permission signal when a predetermined target is settled in an irradiation permission range, and
wherein the display controller is configured to cause the display to display the irradiation permission range in a manner of being superimposed on the fluoroscopic image and change a color of a frame indicating the irradiation permission range when the irradiation permission signal is output.

14. The medical apparatus according to claim 5,
wherein the output controller is configured to output the irradiation permission signal when a predetermined target is settled in an irradiation permission range, and
wherein the display controller is configured to cause the display to display the irradiation permission range in a manner of being superimposed on the fluoroscopic image and change a hue or brightness of any of an inner region or an outer region of the irradiation permission range when the irradiation permission signal is output.

15. The medical apparatus according to claim 1, further comprising:
a notifier configured to issue notification by a sound or a vibration when the irradiation permission signal is output.

16. A control method executed by a medical apparatus, comprising:
acquiring a fluoroscopic image of an object from an imager which performs imaging by irradiating the object with an electromagnetic wave to generate a fluoroscopic image,
correcting an image of one or more predetermined regions used for identifying a target position of the object in the fluoroscopic image based on one or more correction values but not correcting an image of at least a part of a region out of the predetermined region in the fluoroscopic image,
identifying the target position based on the corrected image,
outputting an irradiation permission signal to a therapeutic device which irradiates the object with a therapeutic beam based on the identified target position, and
setting a search region with respect to the acquired fluoroscopic image, and
wherein an image of the set search region is corrected but an image of a region out of the set search region in the fluoroscopic image is not corrected.

17. The medical apparatus according to claim 1, wherein the search region setter is configured to set the search region with respect to the fluoroscopic image based on a manual operation performed by an operator.

18. A medical apparatus comprising:
an acquirer configured to acquire a fluoroscopic image of an object from an imager which performs imaging by irradiating the object with an electromagnetic wave to generate a fluoroscopic image;
a corrector configured to correct an image of one or more predetermined regions used for identifying a target position of the object in the fluoroscopic image based on one or more correction values but does not correct an image of at least a part of a region out of the predetermined region in the fluoroscopic image;
an identifier configured to identify the target position based on an image corrected by the corrector;
an output controller configured to output an irradiation permission signal to a therapeutic device which irradiates the object with a therapeutic beam based on the target position identified by the identifier; and
a display controller configured to:
  cause a display to display a screen for displaying an image corrected by the corrector,
  output the irradiation permission signal when a predetermined target is settled in a irradiation permission range, and
  cause the irradiation permission range to be displayed in a manner of being superimposed on an image corrected by the corrector.

* * * * *